(12) United States Patent
Chuter et al.

(10) Patent No.: US 9,358,097 B2
(45) Date of Patent: Jun. 7, 2016

(54) ILIAC LEG EXTENSION STENT GRAFT

(75) Inventors: Timothy A. M. Chuter, San Francisco, CA (US); Roy K. Greenberg, Bratenahl, OH (US)

(73) Assignees: The Cleveland Clinic Foundation, Cleveland, OH (US); Cook Medical Technologies LLC, Bloomington, IN (US)

( * ) Notice: Subject to any disclaimer, the term of this patent is extended or adjusted under 35 U.S.C. 154(b) by 551 days.

(21) Appl. No.: 12/295,203

(22) PCT Filed: Mar. 29, 2007

(86) PCT No.: PCT/US2007/007577
§ 371 (c)(1),
(2), (4) Date: Dec. 14, 2009

(87) PCT Pub. No.: WO2007/123633
PCT Pub. Date: Nov. 1, 2007

(65) Prior Publication Data
US 2010/0100168 A1 Apr. 22, 2010

Related U.S. Application Data

(60) Provisional application No. 60/786,935, filed on Mar. 29, 2006.

(51) Int. Cl.
*A61F 2/07* (2013.01)
*A61F 2/06* (2013.01)
*A61F 2/89* (2013.01)

(52) U.S. Cl.
CPC ... *A61F 2/07* (2013.01); *A61F 2/89* (2013.01); *A61F 2002/067* (2013.01); *A61F 2002/075* (2013.01)

(58) Field of Classification Search
CPC .................. A61F 2002/065; A61F 2002/067; A61F 2002/068
USPC .................. 623/1.16, 1.31, 1.35, 1.13, 1.14
See application file for complete search history.

(56) References Cited

U.S. PATENT DOCUMENTS

| | | | | |
|---|---|---|---|---|
| 6,344,056 B1 * | 2/2002 | Dehdashtian | ............. | A61F 2/07 623/1.35 |
| 6,409,756 B1 * | 6/2002 | Murphy | ...................... | 623/1.35 |
| 6,524,336 B1 * | 2/2003 | Papazolgou | ............. | A61F 2/07 623/1.16 |
| 6,645,242 B1 * | 11/2003 | Quinn | ...................... | A61F 2/07 623/1.13 |
| 7,014,653 B2 * | 3/2006 | Ouriel | ...................... | A61F 2/07 623/1.14 |

(Continued)

FOREIGN PATENT DOCUMENTS

| | | | | |
|---|---|---|---|---|
| EP | 1 325 717 A2 | 7/2003 | ................ | A61F 2/06 |
| WO | WO 00/42947 | 7/2000 | ................ | A61F 2/06 |

(Continued)

*Primary Examiner* — Yashita Sharma
*Assistant Examiner* — Seema Mathew
(74) *Attorney, Agent, or Firm* — Brinks Gilson & Lione

(57) ABSTRACT

A stent graft leg extension (10) to extend from a bifurcated aortic stent graft into an iliac artery. The stent graft has a tubular body. (12) of a biocompatible graft material and a plurality of self-expanding stents (14) joined to and supporting the tubular body. An uncovered tubular self-expanding stent assembly (26) extends from a first end of the tubular body and is fastened thereto. The uncovered tubular self-expanding stent assembly (26) provides a smooth transition from the leg extension into the iliac artery to reduce the chance of kinks causing problems in the leg extension.

15 Claims, 3 Drawing Sheets

(56) References Cited

U.S. PATENT DOCUMENTS

| | | | |
|---|---|---|---|
| 7,144,421 B2 * | 12/2006 | Carpenter et al. | 623/1.31 |
| 7,294,147 B2 * | 11/2007 | Hartley | A61F 2/07 623/1.13 |
| 7,771,467 B2 * | 8/2010 | Svensson | A61F 2/07 623/1.24 |
| 7,846,194 B2 * | 12/2010 | Hartley et al. | 623/1.13 |
| 2002/0198587 A1 * | 12/2002 | Greenberg | A61F 2/07 623/1.13 |
| 2003/0120333 A1 * | 6/2003 | Ouriel et al. | 623/1.14 |
| 2003/0199967 A1 * | 10/2003 | Hartley et al. | 623/1.13 |
| 2004/0117003 A1 * | 6/2004 | Ouriel | A61F 2/07 623/1.35 |
| 2004/0176832 A1 * | 9/2004 | Hartley et al. | 623/1.11 |
| 2004/0254628 A1 * | 12/2004 | Nazzaro | A61F 2/07 623/1.13 |
| 2006/0095118 A1 | 5/2006 | Hartley | |
| 2006/0136046 A1 | 6/2006 | Hartley et al. | |
| 2006/0178733 A1 * | 8/2006 | Pinchuk | A61F 2/07 623/1.35 |
| 2006/0229707 A1 * | 10/2006 | Khoury | A61F 2/07 623/1.16 |
| 2006/0287704 A1 * | 12/2006 | Hartley | A61F 2/07 623/1.13 |
| 2007/0010874 A1 * | 1/2007 | Sun | 623/1.35 |
| 2008/0208312 A1 * | 8/2008 | Kwitkin | A61F 2/07 623/1.15 |

FOREIGN PATENT DOCUMENTS

| | | | | |
|---|---|---|---|---|
| WO | WO 03/053286 A2 | 7/2003 | | A61F 2/06 |
| WO | WO 2004/049978 A1 | 6/2004 | | A61F 2/06 |

* cited by examiner

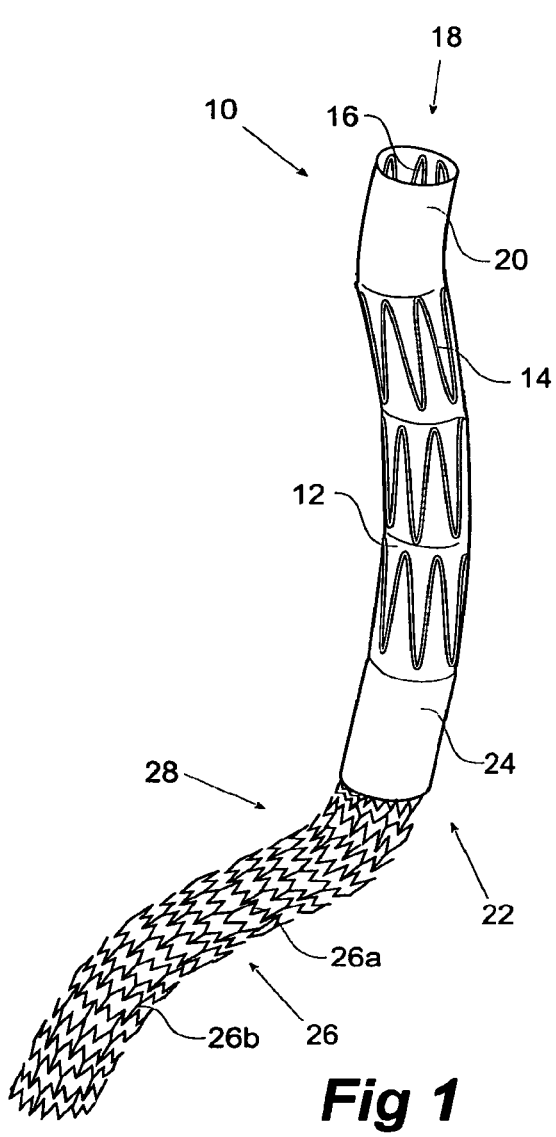
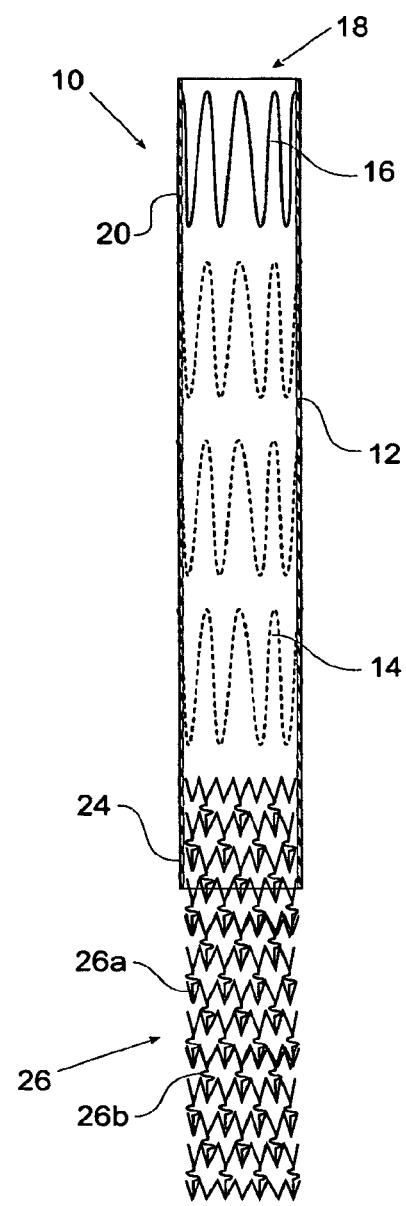
Fig 1
Fig 2

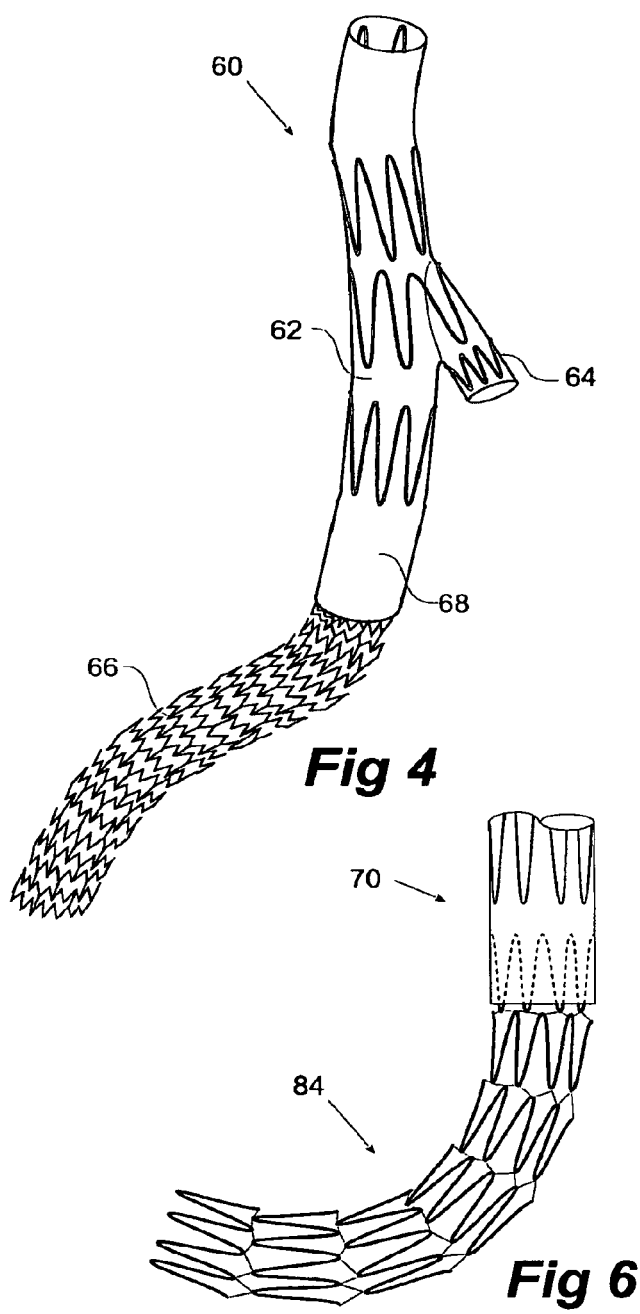
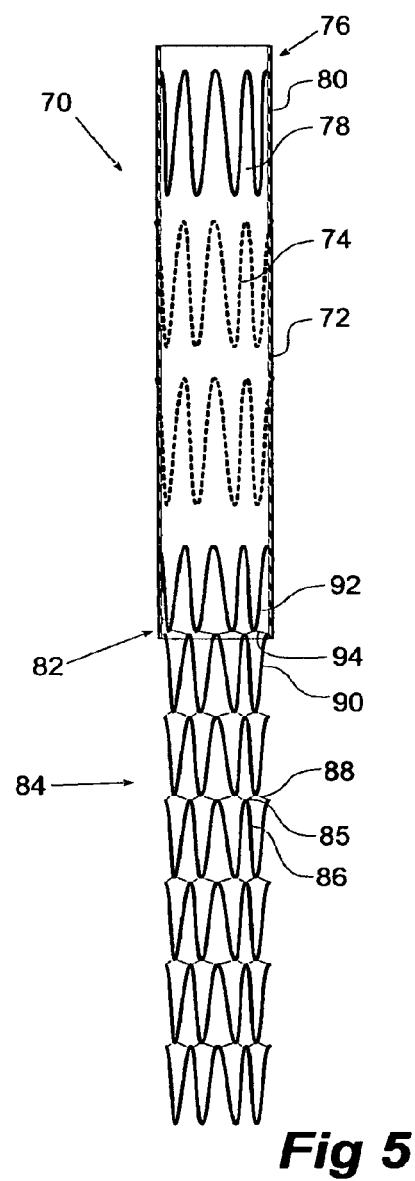
Fig 4
Fig 5
Fig 6

ILIAC LEG EXTENSION STENT GRAFT

TECHNICAL FIELD

This invention relates to a medical device and more particularly to a medical device for use in relation to endovascular surgery.

BACKGROUND OF THE INVENTION

Bifurcated stent grafts are well known for treating abdominal aortic aneurysms. Such stent grafts typically include a tubular body which extends in the aorta towards the renal arteries of a patient and a bifurcation. The bifurcation usually has a shorter leg and a longer leg. Once the bifurcated graft is deployed, an extension leg is provided to extend down one iliac artery from the shorter leg, with the longer leg extending down the other iliac artery.

There can be problems with such stent grafts, however, for example in cases in which the iliac artery is extremely convoluted, as is often the case with older patients. The extension leg provided to extend down one iliac artery from the shorter leg of the bifurcated aortic stent graft can be kinked in the convoluted region, thereby blocking off blood flow to the iliac and femoral arteries. In some instances the iliac artery can kink immediately beyond the end of the extension leg, again causing blood flow restriction.

WO 03/053286 describes an endovascular prosthesis including a first end, a furcated second end, and an anchoring means. The first end has a longitudinally extending central lumen and means for laterally supporting the first end. The furcated second end includes at least two branches that extend from an intersection of the furcated second end. Each of the branches includes a longitudinal support means and a branch lumen in fluid communication with the central lumen of the first end. The anchoring means secures the first end within a vasculature.

SUMMARY OF THE INVENTION

The present invention seeks to provide a stent graft in which the potential for either of these kinking problems can be reduced or at least provide the physician with a useful alternative device.

Throughout this specification the term distal with respect to a portion of the aorta, a deployment device or a prosthesis means the end of the aorta, deployment device or prosthesis further away in the direction of blood flow from the heart and the term proximal means the portion of the aorta, deployment device or end of the prosthesis nearer to the heart. When applied to other vessels similar terms such as caudal and cranial should be understood.

According to an aspect of the present invention there is provided a stent graft device as specified in claim 1.

The invention provides a leg extension stent graft device with a flexible uncovered self-expanding stent tail which can assist with controlling convolutions along the length of the iliac artery. The uncovered stent portion of the leg extension can assist in preventing any convolutions in the artery from forming kinks in the covered tubular body portion of the leg extension. The uncovered section can bend to take up any convolution without kinking whereas the same amount of bending in a covered tubular body could cause kinking.

In one embodiment, the uncovered tubular self-expanding stent assembly comprises, a plurality of zigzag self-expanding stents flexibly linked together. The flexible linking together can be by use of a suture thread tied to alternate apices of adjacent zig-zag stents to provide a degree of flexibility between adjacent stents.

In an embodiment, the uncovered tubular self-expanding stent assembly may comprise a shape memory metal tube integrally formed into a plurality of circumferential stent portions and longitudinal flexible links between the stent portions. The shape memory metal can be Nitinol™. Such a self-expanding stent may for instance be a Zilver™ Stent sold by Cook Incorporated, Bloomington, Ind., USA.

The plurality of self-expanding stents joined to the tubular body can comprise zig-zag Gianturco™ stents.

Preferably, a second end of the tubular body opposite to the first end is provided with an outside sealing surface and at least one self-expanding stent within the tubular body at the second end, in order to assist with sealing of the leg extension device into one of the legs of a bifurcated stent graft deployed into the aortic bifurcation.

In use, the distal end is preferably the first end of the device and the proximal end is the second end of the device.

The uncovered tubular self-expanding stent assembly can extend within the tubular body for a distance equivalent to at least the diameter of the tubular body, in order to assist with providing a stable transition from the covered body portion to the uncovered portion.

The uncovered tubular self-expanding stent assembly extending from a first end of the tubular body can have an exposed length equivalent to between a quarter of the length of the tubular body to equal to the length of the tubular body.

In one embodiment of the invention, the tubular body can comprises a side arm extending therefrom. The side arm can be used for deployment of an extension piece for connecting the internal iliac artery of a patient where the leg extension device is deployed into the common iliac artery and the uncovered portion extends down the external iliac artery towards the femoral arteries.

The tubular body can have a diameter of from 10 mm to 20 mm and a length of about 60 mm to 120 mm and the tubular side branch, if present, can have a length of about 25 mm and a diameter of 8 mm. The exposed portion of the uncovered tubular self-expanding stent assembly can have a length of from 15 mm to 120 mm and a diameter of from 10 mm to 20 mm. Hence the overall length of the stent graft leg extension device can be from 75 mm to 240 mm.

The biocompatible material from which the tubular body is formed is preferably non-porous so that it does not leak or sweat under physiologic forces. The graft material is preferably made of woven or knitted polyester (Vascutek Ltd., Renfrewshire, Scotland, UK). Other biocompatible fabrics, non-woven materials and porous sheets may be used as the graft material. Examples of biocompatible polymers from which porous sheets can be formed include polyesters, such as poly(ethylene terephthalate), polylactide, polyglycolide and copolymers thereof; fluorinated polymers, such as PTFE, expanded PTFE and poly(vinylidene fluoride); polysiloxanes, including polydimethyl siloxane; and polyurethanes, including polyetherurethanes, polyurethane ureas, polyetherurethane ureas, polyurethanes containing carbonate linkages and polyurethanes containing siloxane segments. In addition, materials that are not inherently biocompatible may be subjected to surface modifications in order to render the materials biocompatible. Examples of surface modifications include graft polymerization of biocompatible polymers from the material surface, coating of the surface with a crosslinked biocompatible polymer, chemical modification with biocompatible functional groups, and immobilization of a compatibilizing agent such as heparin or other substances. Thus, any polymer that may be formed into a porous sheet can be used to make a graft material, provided the final porous material is biocompatible. Polymers that can be formed into a porous sheet include polyolefins, polyacrylonitrile, nylons, polyaramids and polysulfones, in addition to polyesters, fluorinated polymers, polysiloxanes and polyurethanes as listed above. Preferably the porous sheet is made of one or more polymers that do not require treatment or modification to be biocompatible. The graft material may include a biocompatible polyurethane. Examples of biocompatible polyurethanes include THORALON® (Thoratec, Pleasanton, Calif.), BIOSPAN®, BIONATE®, ELASTHANE™, PURSIL™ and CARBOSIL™ (Polymer Technology Group, Berkeley, Calif.). As described in U.S. Patent Application Publication No. 2002/0065552 A1, incorporated herein by reference, THORALON® is a polyetherurethane urea blended with a siloxane-containing surface modifying additive. Specifically, the polymer is a mixture of base polymer BPS-215 and an additive SMA-300.

The graft material may also include extracellular matrix materials. The "extracellular matrix" is a collagen-rich substance that is found in between cells in animal tissue and serves as a structural element in tissues. It is typically a complex mixture of polysaccharides and proteins secreted by cells. The extracellular matrix can be isolated and treated in a variety of ways. Following isolation and treatment, it is referred to as an "extracellular matrix material," or ECMM. ECMMs may be isolated from submucosa (including small intestine submucosa), stomach submucosa, urinary bladder submucosa, tissue mucosa, renal capsule, dura mater, liver basement membrane, pericardium or other tissues. Purified tela submucosa, a preferred type of ECMM, has been previously described in U.S. Pat. Nos. 6,206,931, 6,358,284 and 6,666,892 as a bio-compatible, non-thrombogenic material that enhances the repair of damaged or diseased host tissues. U.S. Pat. Nos. 6,206,931, 6,358,284 and 6,666,892 are incorporated herein by reference. Purified submucosa extracted from the small intestine ("small intestine submucosa" or "SIS") is a more preferred type of ECMM for use with the described embodiments. Another type of ECMM, isolated from liver basement membrane, is described in U.S. Pat. No. 6,379,710, which is incorporated herein by reference. ECMM may also be isolated from pericardium, as described in U.S. Pat. No. 4,502,159, which is also incorporated herein by reference. Irrespective of the origin of the graft material, the graft material can be made thicker by making multi-laminate constructs, for example SIS constructs as described in U.S. Pat. Nos. 5,968,096; 5,955,110; 5,885,619; and 5,711,969. All of these references are incorporated herein by reference.

BRIEF DESCRIPTION OF THE DRAWING

Embodiments of the present invention are described below, by way of example only, with reference to the accompanying drawings, in which:

FIG. 1 shows a first embodiment of leg extension for a vascular stent grafting system according to the present invention;

FIG. 2 shows a cross sectional view of the leg extension shown in FIG. 1;

FIG. 4 shows another embodiment of stent graft leg extension according to the present invention;

FIG. 5 shows a cross sectional view of an embodiment of a leg extension stent graft according to the present invention; and FIG. 6 shows part of the leg extension stent graft of FIG. 5 showing how much bending the stent graft can take.

DETAILED DESCRIPTION

Figure 3:
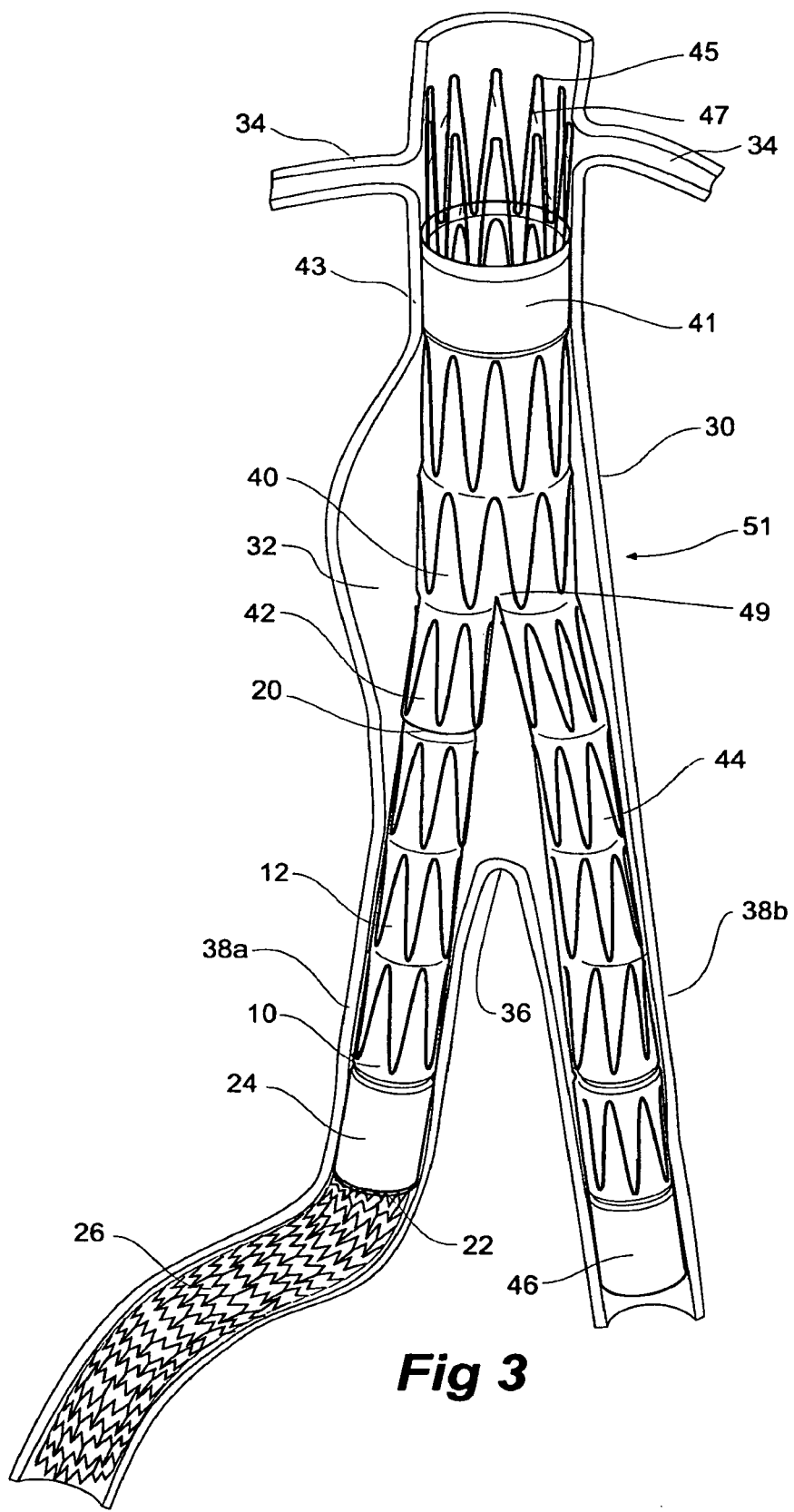
FIG. 3 shows the schematic vasculature of a patient showing how the leg extension according to one embodiment of the present invention can be used within the vasculature.

Now, looking more closely at the drawings and in particular FIGS. 1 and 2, a first embodiment of stent graft according to the present invention is described.

In this embodiment, the stent graft leg extension 10 comprises a tubular body 12 of a biocompatible graft material with a number of zig-zag Gianturco stents 14 on its outer surface between its ends and an inner zig-zag Gianturco stent 16 at the proximal end 18. On the outside of the proximal end, the biocompatible graft material provides a sealing surface 20. At the distal end 22 of the tubular body is another sealing surface 24 and extending from the end 22 is a tubular self-expanding stent 26. The tubular zig-zag stent 26 comprises circumferential zig-zag portions 26a with flexible longitudinal links 26b between the circumferential portions.

As can be seen particularly in FIG. 2, which shows a longitudinal cross-section of the stent graft shown in FIG. 1, the tubular stent 26 extends within the tubular body 12 for at least a length equivalent to one diameter of the tubular body 12 and is suitably fastened, such as by stitching (not shown), inside the tubular body. The length of the tubular stent 26 beyond the distal end 22 of the tubular body 12 is equal to between a quarter to one times the length of the tubular body 12. It will be noted that the tubular stent 26 can take a considerable degree of bending, as shown in FIG. 1, without kinking, whereas an extended tubular body 12 itself may well kink in the region 28 of bent to the same degree.

It will be seen that by this arrangement a flexible transition is provided between the leg extension and the iliac artery.

FIG. 3 shows the use of the leg extension stent graft of FIG. 1 in a vasculature of a patient. FIG. 3 shows a schematic view of the vasculature of a patient, particularly showing the aorta and aortic bifurcation extending down towards the iliac arteries. The vasculature comprises aorta 30 in the region between the renal arteries 34 and the aortic bifurcation 36. Common iliac arteries 38a and 38b extend from the aortic bifurcation 36. The common iliac artery 38a has a considerable kink in it. The aorta 30 has an aneurysm 32 which extends between the renal arteries and the iliac bifurcation.

To traverse the aneurysm, a bifurcated aortic stent graft 40 has been deployed into the aorta 30. The proximal end 41 of the bifurcated stent graft 40 is engaged onto a non-aneurysed portion 43 of the aorta just distal of the renal arteries 34. To ensure good fixation, the stent graft 40 includes a supra renal exposed stent 45 with barbs 47 engaging the wall of the aorta proximal the renal arteries 34.

The stent graft 40 has a short leg 42 and a long leg 44 extending from a bifurcation 49 at its distal end 51. The long leg 44 has a sealing surface 46 at its distal end and this engages in a sealing manner into an non-aneurysed portion of the common iliac artery 38b.

A leg extension 10 of the type shown in FIGS. 1 and 2 has been deployed into the iliac artery 38a with the sealing surface 20 within the shorter leg 42 of the bifurcated stent graft 40 and the leg extension extending down into the iliac artery 38a. The tubular stent 26 allows for a degree of convolution in the iliac artery 38a while still allowing the sealing surface 24 at the distal end 22 of the tubular body 12 of the leg extension 10 to seal conveniently within the iliac artery 38a.

FIG. 4 shows another embodiment of leg extension. In this embodiment the leg extension 60 comprises a tubular body 62 of a graft material with a side arm 64 extending from the tubular body. A tubular self-expanding stent 66 extends from the distal end 68 of the tubular body 62. This leg extension can be used where the internal iliac artery is very close to the aortic bifurcation and the placement of a leg extension without a side arm may cause occlusion of the internal iliac artery. A covered balloon expandable or self-expanding stent (not shown) can be used to extend between the side arm 64 and the internal iliac artery.

FIGS. 5 and 6 shows another embodiment of leg extension in longitudinal cross section with a flexible transition according to the present invention. In this embodiment the leg extension 70 comprises a tubular body 72 of a graft material with a plurality of self-expanding stents 74 on the outside except at the proximal end 76 where the self-expanding stent 78 is on the inside to provide a sealing surface 80 on the outside of the tubular body. At the distal end 82 is a stent assembly 84 which comprises a plurality of self-expanding stents 86 connected together by flexible links 88. In this embodiment the flexible links are formed from a suture tied to alternate apices 85 of adjacent zig-zag stents 86 to provide a degree of flexibility between adjacent stents. The proximal-most uncovered stent 90 of the stent assembly 84 is linked to the distal-most covered stent 92 by a flexible suture thread 94.

FIG. 6 shows that a considerable degree of flexibility is provided by the stent assembly 84 so that a smooth transition is provided for the connection between the vasculature and the leg extension 70.

Throughout this specification various indications have been given as to the scope of this invention but the invention is not limited to any one of these but may reside in two or more of these combined together. The examples are given for illustration only and not for limitation.

Throughout this specification and the claims that follow unless the context requires otherwise, the words 'comprise' and 'include' and variations such as 'comprising' and 'including' will be understood to imply the inclusion of a stated integer or group of integers but not the exclusion of any other integer or group of integers.

The invention claimed is:

1. A stent graft system, comprising:
 a bifurcated stent graft provided with first and second legs, the first and second legs having first and second leg lumens; and
 an elongate leg extension comprising:
  a proximal end,
  a distal end,
  a tubular body of a biocompatible graft material having a proximal end, a distal end and a length between the proximal end and the distal end; and
  a plurality of self extending stents joined to and supporting the tubular body in a longitudinal direction thereof,
  a graft free tubular self-expanding stent assembly having a proximal end, a distal end, a length from the proximal end to the distal end, and a proximal end length, the graft free tubular self-expanding stent assembly comprising a plurality of circumferential zig zag portions connected by longitudinally extending links,
  wherein the proximal end length extends into an inner lumen of a leg of the tubular body for at least a length equal to the diameter of the leg, and is fixedly fastened within the inner lumen of the leg of the tubular body by a fastening mechanism,
  wherein the length of the portion of the graft free tubular self-expanding stent assembly that extends into the tubular body for at least a length equivalent to one diameter of the tubular body and the length of the of the portion of the graft free tubular self expanding stent assembly that extends from the tubular body is equal to between a quarter to one times the length of the tubular body, and
  wherein the graft free tubular self-expanding stent assembly is configured to resist kinking upon bending of the graft free tubular self-expanding stent assembly and has greater kink resistance than the leg.

2. The bifurcated stent graft device of claim 1, wherein the uncovered tubular self-expanding stent assembly comprises a shape memory metal tubular element monolithically formed into a plurality of stents and links between the stents.

3. The bifurcated stent graft device of claim 1, wherein the tubular body of the leg extension is provided with an outside sealing surface at the proximal end thereof and at least one self-expanding stent within the tubular body at the proximal end.

4. The bifurcated stent graft device of claim 1, wherein the uncovered tubular self-expanding stent assembly extends within the tubular body for a distance equivalent to at least the diameter of the tubular body.

5. The bifurcated stent graft device of claim 1, wherein the tubular body of the elongate leg extension comprises a side arm extending therefrom between the proximal and distal ends of the tubular body of the elongate leg extension.

6. The bifurcated stent graft device of claim 1, wherein the self-expanding stents are flexibly linked together by flexible links formed from a suture tied to alternate apices of adjacent stents.

7. A stent graft comprising an elongate tubular main body of a biocompatible graft material and a plurality of self-expanding stents joined to and supporting the tubular main body,
 the tubular main body further comprising
  a proximal end,
  a distal end,
  an inner lumen between the proximal end and the distal end,
  a side arm extending from the tubular main body between the proximal end and the distal end, and at an angle to the tubular main body, and
  an elongate extension at and extending from the distal end of the tubular main body,
  the elongate extension having a proximal end, a proximal end portion having a length, and a distal end,
  the elongate extension extending from inside the lumen of the tubular main body to outside the tubular main body, and fixedly attached to the tubular main body inside the lumen of the tubular main body;
  the elongate extension comprising a graft-free self-expanding stent assembly of stent rings and flexibly linked together, where at least the length of the proximal end portion of the elongate extension extends into the lumen of the tubular main body and is fixedly attached within the lumen,
  wherein the length of the portion of the graft free tubular self-expanding stent assembly that extends into the tubular body is for at least a length equivalent to one diameter of the tubular body and the length of the of the portion of the graft free tubular self expanding stent assembly that extends from the tubular body is equal to between a quarter to one times the length of the tubular body, and
  wherein the graft free tubular self-expanding stent assembly is configured to resist kinking upon bending of the graft free tubular self-expanding stent assembly and has greater kink resistance than the leg.

8. The stent graft device of claim 7, wherein the graft-free self-expanding stent assembly comprises a plurality of zig-zag self-expanding stent portions flexibly linked together by longitudinal links between the stent portions.

9. The stent graft device of claim 8, wherein the graft-free self-expanding stent assembly comprises a shape memory metal tubular element monolithically formed into the plurality of stent portions and the longitudinal links between the stent portions.

10. The stent graft device of claim 7, wherein the plurality of self-expanding stents joined to the tubular main body comprise zig-zag self-expanding stents.

11. The stent graft device of claim 7, wherein the tubular main body is provided with an outside sealing surface at the proximal end thereof and at least one self-expanding stent within the tubular main body at the proximal end.

12. The stent graft device of claim 7, wherein the graft-free self-expanding stent assembly extends within the lumen of the tubular main body for a distance equivalent to at least the diameter of the tubular main body at the distal end.

13. The stent graft device of claim 7 wherein a distal portion of the distal end of the tubular main body is unstented.

14. The system of claim 1 wherein a leg of the tubular main body has a stent free sealing zone and wherein the proximal end length extends into the inner lumen of the leg of the tubular body for at least the length of the stent free sealing zone.

15. A stent graft comprising:
an elongate tubular body comprising:
a proximal end,
a distal end,
a diameter,
a covering of a biocompatible graft material from the proximal end to the distal end, and a plurality of self extending stents joined to and supporting the covered elongate tubular body from the proximal end to the distal end;
a graft free stent portion extending from the distal end of the elongate tubular body, the graft free stent portion having a proximal end, a distal end, a length from the proximal end to the distal end, and a proximal end portion length, the graft free stent portion comprising a plurality of circumferential stents connected by flexible links,
wherein the proximal end length portion of the graft free stent portion extends into an inner lumen the elongate tubular body at the distal end of the elongate tubular body for at least a length equal to the diameter of the elongate tubular, and is fixedly and permanently fastened within the inner lumen of and to an inner surface of the elongate tubular body by a fastening mechanism,
wherein the length graft free stent portion that extends into the lumen of the elongate tubular body extends for at least a length equivalent to one diameter of the elongate tubular body and the length of the of length of the graft free stent portion that extends from the distal end of the elongate tubular body is equal to between a quarter to one times the length of the elongate tubular body, and
wherein graft free stent portion is configured to resist kinking upon bending of the graft free stent portion and has greater kink resistance than the elongate tubular body.

* * * * *